(12) United States Patent
Dener et al.

(10) Patent No.: US 6,187,923 B1
(45) Date of Patent: Feb. 13, 2001

(54) PROCESS FOR THE SYNTHESIS OF QUINAZOLINONES

(75) Inventors: Jeffrey Mark Dener, San Mateo; Cuong Quoc Ly, San Francisco, both of CA (US)

(73) Assignee: Axys Advanced Technologies, Inc., South San Francisco, CA (US)

( * ) Notice: Under 35 U.S.C. 154(b), the term of this patent shall be extended for 0 days.

(21) Appl. No.: 09/435,517

(22) Filed: Nov. 8, 1999

Related U.S. Application Data

(60) Provisional application No. 60/107,680, filed on Nov. 9, 1998.

(51) Int. Cl.[7] .................................................. C07D 239/90
(52) U.S. Cl. ........................................... 544/284; 544/287
(58) Field of Search ...................................... 544/284, 287

(56) References Cited

PUBLICATIONS

Okumura et al., "4–Oxo–1,2,3,4–tetrahydroquinazolines. 3. Synthesis and Choleretic Activity of Quinazoline Derivatives," J. Med. Chem. vol. 5, No. 5:518–532 (1972).

Ozaki et al., "Studies on 4(1H)–Quinazolinones. 5. Synthesis and Antiinflammatory Activity of 4(1H)–Quinazolinone Derivatives," J. Med. Chem vol. 28, No. 5:568–576 (1985).

Yale et al., "Substituted 2,3–Dihydro–4(1H)–quinazolinones. A New Class of Inhibitors of Cell Multiplication," J. Med. Chem vol. 10, No. 3:334–336 (1967).

Primary Examiner—Mukund J. Shah
Assistant Examiner—Hong Liu
(74) Attorney, Agent, or Firm—Vinit G. Kathardekar

(57) ABSTRACT

The present invention provides a process for synthesizing a compound or a library of compounds of Formula 1A and 1B:

Formula 1A

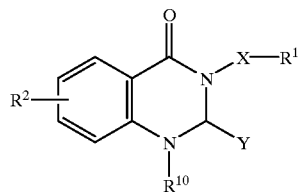

Formula 1B

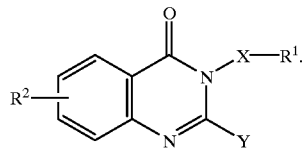

12 Claims, No Drawings

PROCESS FOR THE SYNTHESIS OF QUINAZOLINONES

This application claims benefit to U.S. provisional 60/107,680 filed Nov. 9, 1998.

FIELD OF INVENTION

The present invention relates to a process for the synthesis of Quinazolinones having potential biological activity.

BACKGROUND OF THE INVENTION

A variety of substituted quinazolinones have been reported in the literature These Quinazolinones are known to be biologically active. One such class of Quinazolinones is 2,3-dihydro-4(1 H)-quinazolinones. It has been reported that these Quinazolinone compounds were studied for their pharmacodynamic, insecticidal, and antifungal activity.

Other studies, for example as reported by Yale and Kalkstein in J. Med. Chem. 10(3), 334–336, suggest that the 2,3-Dihydro-4(1 H)-Quinazolinones were effective inhibitors of multiplication of the Earle's L cell line. Quinazolinone derivatives were also shown to act as cholerectic agents useful in the treatment of cholelthiasis and jaundice, as reported by Okuura et. al. in J. Med. Chem., 1972, Vol. 15, No. 5, 518–532. It has also been reported by Ozaki et. al. in J. Med. Chem., 1985, 28, 568–576, that the 4(1 H)-Quinazolinones were studied as potent antiinflammatory agents.

Given the wide spread utility of the Quinazolinone compounds, there is a continuing need to synthesize Quinazolinone compounds. Traditional synthetic methods are time consuming and can only make these compounds on an individual basis. There is thus a need for a synthetic process which will produce a large number (library) of such Quinazolinone compounds in a rapid manner.

SUMMARY OF THE INVENTION

The present invention provides a process for synthesizing a compound or a library of compounds represented by Formula 1A and 1B:

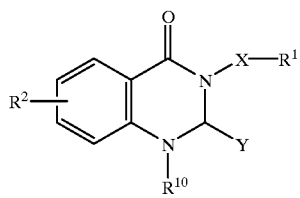

Formula 1A

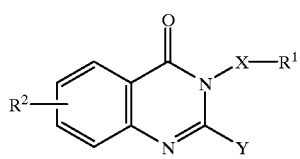

Formula 1B wherein:

$R^1$ is selected from a group consisting of —$C_{1-10}$ alkyl, —$OC_{1-4}$ alkyl, —$C_{4-10}$ saturated or partially unsaturated cyclo alkyl, heteroaryl, aryl substituted with $R^3$, $R^4$, and $R^5$, and —$C_{1-4}$ alkyl substituted with one or more of aryl or heteroaryl;

$R^2$ is selected from H, —$C_{1-4}$ alkyl, —COOH, —$COOC_{1-4}$ alkyl, —$NO_2$, —$NH_2$, —$C_{4-8}$ alkyl-C(O)—$NH_2$, —$NHC_{1-6}$ alkyl, aryl-C(O)—$NH_2$, —CN, —O—$C_{1-4}$ alkyl, and halogen;

X represents —$(CH_2)_{1-4}$—;

Y represents —$C_{1-6}$ alkyl, —$C_{4-10}$ cycloalkyl, or aryl substituted with $R^6$, $R^7$, and $R^8$; $R^3$, $R^4$, and $R^5$ independently at each occurrence represent H, —$CF_3$, —$OCF_3$, halogen, —$OC_{1-4}$ alkyl or —$C_{1-6}$ alkyl;

$R^6$, $R^7$, and $R^8$ independently at each occurrence represent H, —O—$C_{1-4}$ alkyl, alkyl, —O—Ph—O-alkyl, —O—Ph-alkyl, —Ph, halogen, or —CN; alternatively when $R^6$ and $R^7$ along with the phenyl ring to which they are attached represent

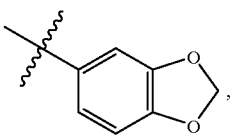

$R^8$ is H; and $R^{10}$ represents H, $C_1$–$C_4$ alkyl, benzyl, substituted benzyl, $C_2$–$C_6$ alkelene, substituted alkyl, or —$(CH_2)_{1-3}$-$COOC_{1-4}$ alkyl; said process comprising the steps of:

(i) reacting an aldehyde of Formula A

Y—CHO           Formula A, with an amine of Formula B

$R^2$-X—$NH_2$           Formula B, wherein $R^2$, X, and Y are as defined above, to yield a compound of Formula C Formula C

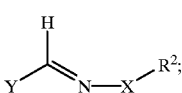

(ii) reacting the compound of Formula C with a compound of Formula D

Formula D

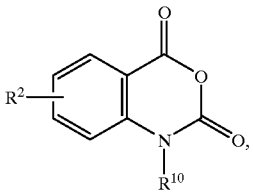

to yield a compound of Formula 1A

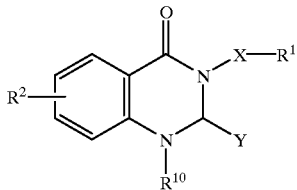

Formula 1A where $R^1$, $R^2$, $R^{10}$ and Y are as defined above; and (iii) optionally oxidizing a compound of Formula 1A, when $R^{10}$ is H, followed by treating with an aminomethyl polystyrene resin, to yield a compound of Formula 1B.

Another aspect of the present invention provides a process for synthesizing a compound or a library of compounds represented by Formula 1A:

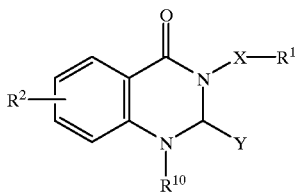

Formula 1A wherein X, Y, $R^1$, $R^2$ and $R^{10}$ are as defined above, said process comprising:

reacting a compound of Formula C

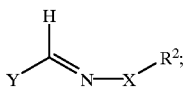

Formula C with a compound of Formula D

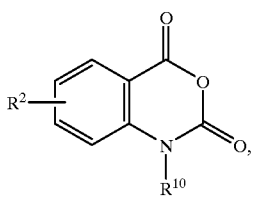

Formula D followed by optional treatment with an aminoalkyl, preferably aminomethyl, polystyrene resin to yield a compound of Formula 1A.

In yet another aspect of the present invention is provided a process for synthesizing of a compound or a library of compounds of Formula 1B

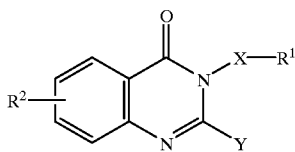

Formula 1B wherein:
$R^1$, $R^2$, X, Y, are as defined above, and $R^{10}$ represents H, said process comprising:
oxidizing a compound of Formula 1A,

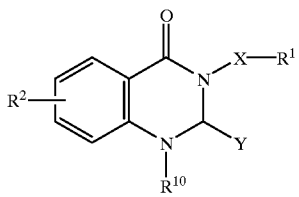

Formula 1A followed by treating with an aminomethyl polystyrene resin, to yield a compound of Formula 1B.

DETAILED DESCRIPTION OF THE INVENTION

Step (i) of the process of the present invention may be performed successfully using either solutions or suspensions of the aldehyde of Formula A or the amine of Formula B. However preferred embodiments of the present invention provide a process wherein step (i) comprises using solutions of the aldehyde of Formula A, and the amine of Formula B. Illustrative examples of solvents which may be used to prepare the solutions of the aldehyde of Formula A and the amines of Formula B are acids, protic solvents, and polar solvents. Preferred acid solvents are acetic acid, and propionic acid. Preferred protic solvents are methanol and ethanol. Preferred polar solvents are DMF, DMSO, and dioxane. A further preferred embodiment provides a process wherein step (i) comprises using at least one of an acetic acid, or a propionic acid solution of the aldehyde of Formula A and the amine of Formula B. The foregoing signifies that the process of the preferred embodiment comprises at least a solution of the aldehyde and the amine in acetic acid or propionic acid, but can comprise a mixture of the two with or without additional solvents.

Another preferred embodiment provides a process wherein step (ii) comprises reacting an acetic acid solution of a compound of Formula C with a solution of a compound of Formula D. Preferably the solution of a compound of Formula D is prepared using at least one solvent selected from the group consisting of DMF, DMSO, dioxane, methylene chloride, acetic acid, chloroform, THF, and propionic acid. Particularly preferred solvents for preparing the solution of a compound of Formula D are at least one of acetic acid, methylene chloride, THF, and DMF.

Yet another preferred embodiment provides a process wherein step (iii) comprises oxidizing a compound of Formula 1A using iodine, $KMnO_4$, or $DDQ/CHCl_3$ suspension. Also provided in another preferred embodiment of the present invention is a process wherein $R^1$ is selected from a group consisting of —$C_{1-6}$ alkyl, —$OC_{1-4}$ alkyl, —$C_{4-6}$ saturated or partially unsaturated cyclo alkyl, heteroaryl, aryl substituted with $R^3$, $R^4$, and $R^5$, or —$C_{1-4}$ alkyl substituted with one or more of aryl or heteroaryl; $R^2$ is selected from H, —$C_{1-4}$ alkyl, —O—$C_{1-4}$ alkyl, and halogen; Y represents —$C_{1-4}$ alkyl, or aryl substituted with $R^6$, $R^7$, and $R^8$; $R^3$, $R^4$, and $R^5$ independently at each occurrence represent H, —O—$C_{1-4}$ alkyl, —$CF_3$, halogen, or —$C_{1-4}$ alkyl; $R^6$, $R^7$, and $R^8$ independently at each occurrence represent H, —O—$C_{1-4}$ alkyl, —$C_{1-4}$ alkyl, —O—Ph— O—$C_{1-4}$ alkyl, —Ph, or halogen; or when $R^6$ and $R^7$ along with the phenyl ring to which they are attached represent

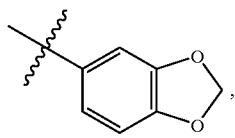

$R^8$ is H; and $R^{10}$ represents —$C_{1-2}$ alkyl, —$C_{1-2}$-Ph or —$CH_2$-COO—$C_2H_5$.

A further preferred embodiment of the present invention provides a process wherein $R^1$ represents

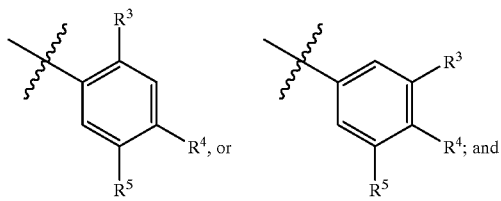

Y represents

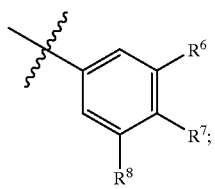

wherein $R^3$, $R^4$, $R^5$, $R^6$, $R^7$ and $R^8$ are as defined in the summary of the invention.

Another aspect of the present invention provides a library of compounds synthesized by the processes of the present invention.

EXPERIMENTAL DETAILS

General Comments

Both the amines (compounds of Formula B) and aldehydes (compounds of Formula A) are dissolved in acetic acid at a concentration of 0.40 molar and mixed for 1.5–2 hours to allow for imine formation. Next a 0.10 molar solution or suspension of the isatoic anhydride (Formula D) in THF is added and the mixture is heated to about 95°–100°C. in a block heater for 4 hours. Several oxidation conditions are validated for the final oxidation step, e.g., $KMnO_4$/acetone/RT, $I_2$/$CHCl_3$/RT, DDQ/dioxane/RT, etc., but the preferred conditions are DDQ/$CHCl_3$/RT. It was surprisingly found that purification with aminomethyl polystyrene resin removes any unreacted isatoic anhydride, aldehyde, DDQ by-products along with colored impurities, to yield a purer Formula 1B compound.

Amines (Compounds of Formula B), and aldehydes (Compounds of Formula A) are commercially available.

DDQ reagent was obtained from Aldrich. The 1.20 mmol/g loading, 100–200 mesh aminomethyl polystyrene resin was obtained from Midwest Bio-Tech Incorporated.

The following synthetic scheme (Scheme I) generally describes one of the processes of the present invention.

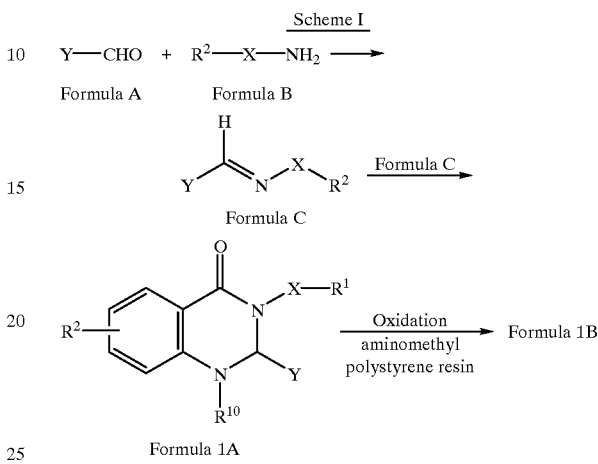

General Description:

The general process for the synthesis of compounds of Formula 1B is as follows:

Step A: Imine (Compound of Formula C) formation: 125 μL of a 0.40 molar solution of the amine (AM, Formula B) in acetic acid (AcOH) was added to a reaction vessel, to which was then added 1 mole equivalent of an aldehyde of Formula A, in acetic acid. This reaction mixture was mixed for about 2 h to yield an imine, a compound of Formula C.

Cyclization of the imines (Compound of Formula C) with isatoic anhydride: To a solution of the imine in acetic acid was added isatoic anhydride (ISA, compound of Formula D) as a THF solution. The resulting reaction mixture was heated under reduced pressure at a temperature of about 100° C., for up to 6 hours. The reaction mixture was cooled to room temperature to yield a compound of Formula 1A. DDQ oxidation and aminomethyl polystyrene resin-mediated purification: A compound of Formula 1A was treated with DDQ/$CHCl_3$ suspension. This reaction mixture was mixed for up to 6 hours to yield a crude mixture of a compound of Formula 1B.

Compounds of Formula 1B were purified by further treatment with aminomethyl polystyrene resin. The reaction mixture comprising a compound of Formula 1B was transferred to another reaction vessel containing aminomethyl polystyrene resin. This mixture was shaken for up to 24 hours. The resin solution was then filtered through silica gel. The silica gel was washed with chloroform. The combined organic solvents were combined, evaporated to yield a compound of Formula 1B.

Isatoic anhydrides (compounds of Formula D) were prepared as shown in the following reaction Scheme II.

Scheme II

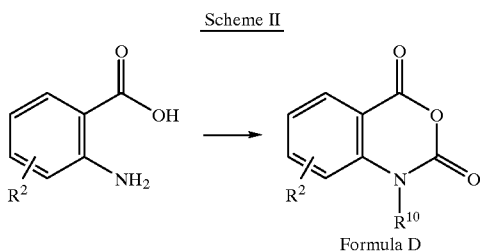

Formula D where $R^2$ and $R^{10}$ are as defined in the summary of the invention.

Isatoic anhydrides, compounds of Formula D, were prepared, as outlined in Scheme II, by treatment of the corresponding commercially available anthranillic acids with phosgene in an inert solvent, preferably toluene. Procedures for the specific isatoic anhydrides syntheses are given below.

5-Methoxyisatoic Anhydride

To a mixture of 10.0 g (60.0 mmol) of 5-methoxyanthranilic acid in 80 mL of 1,4-dioxane was slowly added 100 mL (193 mmol) of a 1.93 molar solution of phosgene, or thiophosgene in an inert solvent, preferably a hydrocarbon solvent such as toluene, at room temperature. The mixture was stirred overnight at room temperature. This mixture was then concentrated in vacuo to a small volume. This concentrated reaction mixture was filtered through silica and the filter cake was washed with hexane to give 10.99 g (95.2%) of the 5-methoxyisatoic anhydride as an off white solid. MS (Cl mode) m/z 176 (M-18, 100%), 194 (M+H, 71%).

5-Methylisatoic Anhydride:

To a mixture of 10.0 g (66.0 mmol) of 5-methylanthranilic acid in 60 mL of 1,4-dioxane was slowly added 100 mL (193 mmol) of a 1.93 molar solution of phosgene in toluene, at room temperature. The mixture was stirred overnight at room temperature, followed by concentration in vacuo to a small volume. The concentrated reaction mixture was filtered through silica and the filter cake was washed with hexane to give 9.81 g (83.7%) of the 5-methylisatoic anhydride as a light yellow solid. MS (Cl mode) m/z 160 (M-18, 100%), 178 (M+H, 71%).

3-Methylisatoic Anhydride:

To a mixture of 10.0 g (66.0 mmol) of 3-methylanthranilic acid in 60 mL of 1,4-dioxane was slowly added 100 mL (193 mmol) of a 1.93 molar solution of phosgene in toluene, at room temperature. The mixture was stirred overnight. The mixture was concentrated in vacuo to yield a residue which was triturated with ethyl acetate-hexane (1:4), filtered, washed with hexane and dried to afford 11.66 g (99.5%) of the 3-methylisatoic anhydride as an off white solid. MS (Cl mode) m/z 160 (M-18, 100%), 178 (M+H, 90%).

5-Chloro-N-methyl Isatoic anhydride:

To a stirred solution of 4.95 g (25.1 mmol) of 5-chloroisatoic anhydride in 80 mL of dry N,N-dimethylformamide (DMF) was added 5.15 g (48.6 mmol) of powdered sodium carbonate forming a suspension. The suspension was then treated with 2.00 mL (4.86 g; 32.1 mmol) of iodomethane. The resulting suspension was stirred for 13 hours, then it was poured into 300 mL of water with vigorous stirring. After 2–3 minutes the resulting precipitate was filtered, and washed with 200 mL of water. The filter cake was dissolved in 200 mL of dichloromethane and this solution was dried ($Na_2SO_4$). The solution was concentrated in vacuo and the residue triturated with ethyl acetate-hexane (1:3). The solid was filtered, washed with ethyl acetate-hexane (1:3), and finally hexane. The solid was dried in vacuo to give 3.90 g (73%) of the title compound as a pale yellow solid. $^1$H NMR (300 MHz, DMSO-D6) d 3.42 (s, 3 H), 7.44 (d, 1 H), 7.85 (d, 1 H0, 7.83, (d, 1 H), 7.92 (d, 1 H). MS (Cl Mode) m/z 212 (M+H, 100%), 240 (M+29, 8%). HPLC analysis showed a single peak.

N-Benzylisatoic Anhydride:

A solution of 5.00 g (22.0 mmol) of N-benzyl anthranillic acid in 30 mL of 1,4-dioxane was briefly cooled in an ice water bath, then 60 mL (116 mmol) of a 1.93 molar solution of phosgene in toluene was added. The solution was stirred for 2 minutes in the ice bath, then it was stirred for 5 hours at room temperature. Nitrogen gas was then passed through the solution for 30 minutes then the reaction mixture was concentrated in vacuo. The residue was dried under high vacuum to give 5.62 g (100%) of N-benzylisatoic anhydride as an off-white solid. $^1$H-NMR (300 MHz, DMSO-D6) d 5.25 (s, 5 H), 7.18–7.39 (m, 7 H), 7.69 (t, 1 H), 7.99 (d, 1 H). MS (Cl Mode) m/z 254 (M+H, 100%), 282 (M+29, 11%). HPLC analysis showed a single peak.

4-Chloroisatoic Anhydride:

To a mixture of 10.0 g (58.0 mmol) of 4-chloroanthranilic acid in 100 mL of 1,4-dioxane was slowly added 100 mL (193 mmol) of a 1.93 molar solution of phosgene in toluene, at room temperature. The mixture was stirred overnight. The mixture was concentrated to yield a residue which was triturated with ethyl acetate-hexane (1:4), filtered, washed with hexane and dried to afford 8.78 g (76.2%) of the 4-chloroisatoic anhydride as a light brown solid. MS (Cl mode) m/z 198 (M+H, 100%), Cl pattern 200, 35%.

3-Methoxyisatoic Anhydride:

To a mixture of 10.0 g (60.0 mmol) of 3-methoxyanthranilic acid in 60 mL of 1,4-dioxane was slowly added 100 mL (193 mmol) of a 1.93 molar solution of phosgene in toluene, at room temperature. The mixture was stirred overnight. The mixture was concentrated to yield a residue which was triturated with ethyl acetate-hexane (1:4), filtered, washed with hexane and dried to afford 11.33 g (98%) of the 3-methoxyisatoic anhydride as an off white solid. MS (Cl mode) m/z 176 (M-18, 100%), 194 (M+H, 53%).

6-Methylisatoic Anhydride:

To a mixture of 10.0 g (66.0 mmol) of 6-methylanthranilic acid in 60 mL of 1,4-dioxane was slowly added 100 mL (193 mmol) of a 1.93 molar solution of phosgene in toluene, at room temperature. The mixture was stirred overnight. The mixture was concentrated to yield a residue which was triturated with ethyl acetate-hexane (1:4), filtered, washed with hexane and dried to afford 11.579 (98.7%) of the 3-methoxyisatoic anhydride as a light brown solid. MS (Cl mode) m/z 160 (M-18,100%),178 (M+H, 95%).

4,5-Dimethoxyisatoic Anhydride:

To a mixture of 10.0 g (51.0 mmol) of 4,5-dimethoxyanthranilic acid in 80 mL of 1,4-dioxane was slowly added 100 mL (193 mmol) of a 1.93 molar solution of phosgene in toluene, at room temperature. The mixture was stirred overnight. The mixture was concentrated to yield a residue which was triturated with ethyl acetate-hexane (1:4), filtered, washed with hexane and dried to afford 11.0 g (97.2%) of the 4,5-dimethoxyisatoic anhydride as a gray solid. MS (Cl mode) m/z 206 (M-18, 100%), 224 (M+H, 51%).

The following compounds were prepared using the process of the present invention. The following procedure is representative.

2-[3-(4-methoxyphenoxy)phenyl]-3-(4-trifluoromethylbenzyl)-6-methoxyquinazolin-4one
(Example 6)

3-(4-methoxyphenoxy)benzylidine-4-trifluoromethylbenzylamine (Compound C)

A mixture of 3-(4-methoxyphenoxy)benzaldehyde (0.4 M solution in 125 mL AcOH, 0.5 mmol), and 4-(trifluoromethyl)benzylamine (0.4 M solution in 125 mL AcOH, 0.05 mmol) was shaken at room temperature for 2 hr to yield the subject compound of Formula C.

Dihydro-(2H)-2-[3-(4-methoxyphenoxy)phenyl]-3-)4-trifluoromethylbenzyl)-6-methoxyquinazoline-4-one (Compound E)

The 3-(4-methoxyphenoxy)benzylidine-4-trifluoromethylbenzylamine, above, was treated with 500 μL (0.05 mmol) of a 0.10 molar mixture of 5-methoxyisatoic anhydride in THF and heated in a preheated heating block at 95°–100° C. for 3.5 hr. The solvent evaporated during the heating period, upon cooling the reaction mixture, the subject compound of Formula 1A was obtained.

2-[3-(4-methoxyphenoxy)phenyl]-3-(4-trifluoromethylbenzyl)-6-methoxyqulnazolin4-one (Example 6): Compound of Formula 1B The Dihydro-(2H)-2-[3-(4-methoxyphenoxy)phenyl]-3-)4-trifluoromethyl benzyl)-6-methoxyquinazoline-4-one, above, was treated with 1.0 mL (0.05 mmol) of 0.05 molar DDQ/CHCl₃ suspension and the mixture shaken at room temperature for 3.5–4 hr. The oxidation product was then purified by resin capture (with about 80 mg of VHL aminomethyl polystyrene resin) overnight. The reaction flask was covered with Teflon film. The resin solution was filtered through 30–50 mg of silica gel, washed with 0.5 mL of chloroform. The product was further purified by Prep TLC eluted with 30% ethyl acetate-hexane to give 9.5 mg (36.5%) of the subject quinazolin-4-one as a white solid. $^{1}$H-NMR (300 MHz, CDCl₃) δ3.82 (s, 3 H), 3.96 (s, 3 H), 5.33 (s, 2 H), 6.80–7.73 (m, 15 H). MS m/z 533 (M+H, 100%).

Using the above procedures the following compounds of Formula 1A were prepared:

EXAMPLE 1

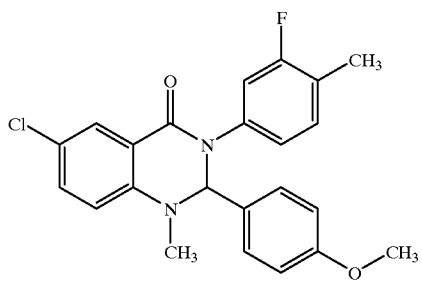

$^{1}$H NMR: (300 MHz, DMSO-d₆) δ2.20 (s, 3 H), 2.85 (s, 3 H), 3.70 (s, 3 H), 6.19 (s, 1 H), 6.68 (d, 1 H), 6.82 (d, 2 H), 6.95 (dd, 1 H), 7.05–7.25 (m, 3 H), 7.24 (t, 1 H), 7.41 (dd, 1 H), 7.72 (d, 1 H)

MS: (m/z, M+H, 100%): Calc.: 410.12; Obs.: 410.9

EXAMPLE 2

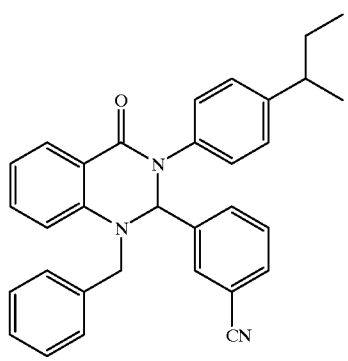

$^{1}$H NMR: (300 MH, DMSO-d₆) δ0.75 (t, 3 H), 1.10 (d,3 H), 1.50 (q, 2 H), 2.55 (m, 1 H), 4.85 (AB q, 2 H), 6.47 (s, 1 H), 6.78–6.84 (m, 2 H), 7.14 (AB q, 4 H), 7.20–7.36 (m, 7 H), 7.53 (t, 1 H), 7.65 (s, 1 H), 7.75 (d, 1 H), 7.80 (dd, 1 H) MS: (m/z, M+H, 100%): Calc.: 471.23; Obs,: 471.5

The following compounds of Formula 1B were prepared using the process of the present invention:

EXAMPLE 3

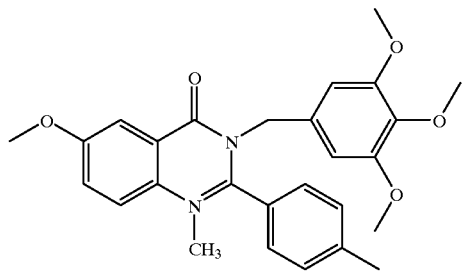

$^{1}$H-NMR (300 MHz, CDCl₃) δ2.45 (s, 3 H), 3.70 (s, 6 H), 3.80, (s, 3 H), 3.95 (s, 3 H), 5.30 (s, 2 H), 6.20 (s, 2 H), 7.25–7.40 (m, 2 H), 7.45 (d, 1 H), 7.70–7.80 (m, 2 H).

MS (m/z, M+H, 100%): Calc.: 446.18; Obs.: 447.1

EXAMPLE 4

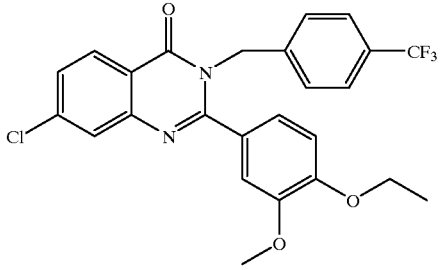

$^{1}$H-NMR (300 MHz, CDCl₃) δ1.55 (t, 3 H), 3.60 (s, 3 H), 4.10 (q, 2 H), 5.40 (s, 2 H), 6.70 (d, 1 H), 6.90–7.00 (m, 2 H), 7.15 (d, 2 H), 7.50–7.60 (m, 3 H), 7.80 (d, 1 H), 8.30 (d,1 H).

MS (m/z, M+H, 100%): Calc.: 488.11; Obs.: 489.1.

EXAMPLE 5

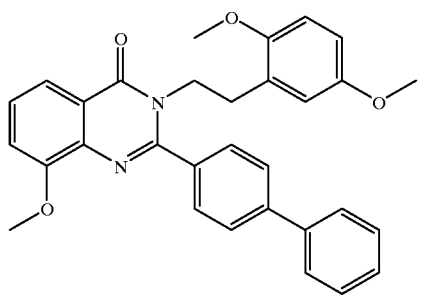

$^1$H-NMR (300 MHz, CDCl$_3$) δ3.00 (t, 2 H), 3.40 (s, 3 H), 3.65 (s, 3 H), 4.00 (s, 3 H), 4.40 (t, 2 H), 6.45 (d, 1 H), 6.60 (d, 1 H), 6.70 (dd, 1 H), 7.20–7.70 (m, 11 H), 8.00 (dd,1 H).

MS (m/z, M+H, 100%): Calc.: 492.2; Obs.: 493.2.

EXAMPLE 6

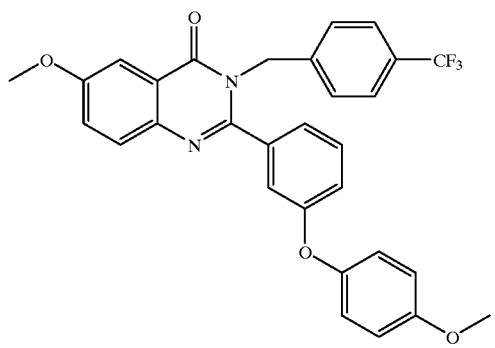

$^1$H-NMR (300 MHz, CDCl$_3$) δ3.82 (s, 3 H), 3.96 (s, 3 H), 5.33 (s, 2 H), 6.73–7.80 (m, 15 H).

MS (m/z, M+H, 100%): Calc.: 532.16; Obs.: 533.0.

EXAMPLE 7

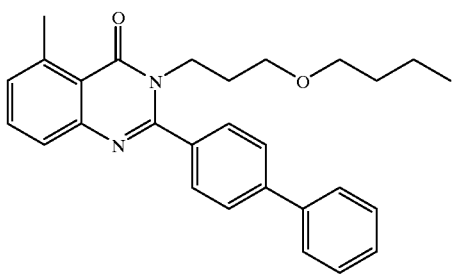

$^1$H-NMR (300 MHz, CDCl$_3$) δ0.80 (t, 3 H), 1.15–1.40 (m, 4 H), 1.85–2.00 (m, 2 H), 2.90 (s, 3 H), 3.15 (t, 2 H), 3.40 (t, 2 H), 4.40 (br t, 2 H), 7.40–7.80 (m, 12 H). MS (m/z, M+H, 100%): Calc.: 426.23; Obs.: 427.1.

EXAMPLE 8

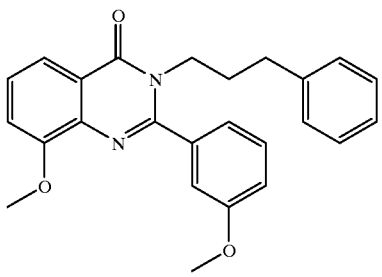

$^1$H-NMR (300 MHz, CDCl$_3$) δ1.95 (br qu, 2 H), 2.55 (t, 2 H), 3.85 (s, 3 H), 4.05 (br t, 2 H), 6.95–7.10 (m, 5 H), 7.15–7.25 (m, 3 H), 7.40 (t, 1 H), 7.55 (dt, 1 H), 7.70–7.85 (m, 2 H), 8.35 (br d, 1 H).

MS (m/z, M+H, 100%): Calc.: 370.17; Obs.: 371.1.

Starting materials (precursors) for the above six compounds are listed in the following Table 1:

| Example | Aldehyde Formula A | Amine Formula B | Isatoic Anhydride Formula D |
|---|---|---|---|
| 1 | 4-methylbenzaldehyde | 3,4,5-trimethoxybenzylamine | 6-methoxy isatoic anhydride |
| 2 | 3-ethoxy-4-methoxybenzaldehyde | 4-(trifluoromethyl)benzylamine | 7-chloro isatoic anhydride |

-continued

| Example | Aldehyde Formula A | Amine Formula B | Isatoic Anhydride Formula D |
|---|---|---|---|
| 3 | biphenyl-CHO | H₂N-CH₂CH₂-(2,5-dimethoxyphenyl) | 8-methoxy isatoic anhydride |
| 4 | 4-methoxyphenoxy-3-CHO-phenyl | H₂N-CH₂-(4-CF₃-phenyl) | 6-methoxy isatoic anhydride |
| 5 | biphenyl-CHO | H₂N-(CH₂)₃-O-(CH₂)₃-CH₃ | 5-methyl isatoic anhydride |
| 6 | 3-methoxybenzaldehyde | H₂N-CH₂CH₂CH₂-phenyl | isatoic anhydride |

Chromatography:

The above examples were analyzed using a Hewlett Packard HP1100 HPLC employing a Zorbax 4.6 mm×7.5 cm SP-C18 column with a guard column. Samples were monitored at UV settings of 214 and 254 nm. The column was heated to about 40° C. and the flow rate was 0.800 mL per minute for all runs. Gradient elution was performed using water with 0.05% TFA (solvent A) and acetonitrile containing 0.05% TFA (solvent B) as mobile phases. Most samples were prepared as dilute solutions in acetonitrile.

HPLC Gradient
Time (minutes) % Solvent B
0.00 1.00
5.00 90.0
5.50 100.0
9.00 100.0
10.00 1.00

Mass Spectrometry:

Identity of peaks observed by HPLC were determined by electrospray (ESI) LC/MS analysis on a Sciex 150 MCA mass spectrometer with a Shimadzu LC-10 HPLC. Most samples were prepared as dilute solutions in acetonitrile or methanol. Compounds were analyzed by direct injection MS analysis was performed on the Sciex 150 MCA mass spectrometer according to the following conditions:

LC/MS Assay:
Injection volume: 10 mL
Column: Zorbax 3.0×50.0 mm column with inline filter
Temperature: 40° C.

Gradient: 0–100% B over 6.0 min, 100% B for 1.0 min, 0% B for
2.0 min.
Mobile Phase 99% water/1% MeOH containing 0.05% AcOH
(Solvent A)
Mobile Phase 99% MeOH/1% water containing 0.05% AcOH (Solvent B)
MS Assay:
Mode: Positive ion ESI
injection volume 10 mL
flow rate 0.3 mL/min, 90% solvent B

DEFINITIONS AND ABBREVIATIONS

As used in the present invention the following terms and abbreviations have the following meaning, unless otherwise indicated.

Library of compounds: This term indicates a collection of independent (individual) compounds that are synthesized by the process of the present invention. Generally the term library of compounds indicates a collection of individual compounds distinct from one another. Also included in the library of compounds is a mixture of the individual compounds.

"Alkyl", or "alkyl radical" is meant to indicate a hydrocarbon moiety of up to 8 carbon atoms, unless indicated otherwise. This hydrocarbon can be saturated or unsaturated, is generally attached to at least one other atom, and can be straight chain, or branched, or cyclic. The term straight chain alkyl is meant to represent an unbranched hydrocarbon moiety of up to 8 carbon atoms. An example of a straight chain alkyl is a n-pentyl group.

The term "cycloalkyl", "cycloalkyl ring", or "cycloalkyl radical" indicates a saturated or partially unsaturated three to ten carbon monocyclic or bicyclic hydrocarbon moiety which is optionally substituted with an alkyl group.

As used in the present invention, the illustration:

generally indicates the point of attachment of the group, comprising the illustration, to another group or atom. The term "protic solvent" represents a solvent that is capable of donating a proton. Illustrative examples are inorganic and organic acids, and alcohols, including methanol, ethanol, propanol, and butanol.

The term "Ph" represents an optionally substituted phenyl radical or group. The term "aryl" means an aromatic monocyclic, bicyclic, or a fused polycyclic hydrocarbon radical containing from 6 to 14 carbon atoms or the number indicated. Thus a $C_6$–$C_4$ aryl group includes phenyl, naphthyl, anthracenyl, etc. The term "heteroaryl" means aryl, as defined above, containing 5–14 atoms of the number indicated wherein one or more of the carbon atoms is replaced by a hetero atom chosen from N, O, and S. The hetero atoms can exist in their chemically allowed oxidation states. Thus Sulfur (S) can exist as a sulfide, sulfoxide, or sulfone. Illustrative examples of heteroaryl groups are thienyl, furyl, pyrrolyl, indolyl, pyrimidinyl, isoxazolyl, purinyl, imidazolyl, pyridyl, pyrazolyl, quinolyl, and pyrazinyl.

"Optional substituents" for aryl, hetero aryl, and Ph groups are independently selected from a group consisting of H, —$NH_2$, halogen, —O—$C_{1-4}$ alkyl, , —$NHC_1$–$C_4$ alkyl, —$N(C_1$–$C_4)_2$ alkyl, $CF_3$, and $C_{1-4}$ alkyl.

"Optional" or "optionally" means that the subsequently described event or circumstance may or may not occur, and that the description includes instances where the event or circumstance occurs and instances in which it does not. For example, the phrase "optionally is substituted with one to three substituents" means that the group referred to may or may not be substituted in order to fall within the scope of the invention.

The term "halogen" represents at least one of chlorine, bromine, iodine, and fluorine radicals. "Inert solvent" as used herein represents solvents which do not react with the reagents dissolved therein. Illustrative examples of inert solvents are tetrahydrofuran (THF), methylene chloride, dichloro methane (DCM), ethyl acetate (EtOAc), dimethyl formamide (DMF), diaoxane, chloroform, and DMSO.

Abbreviations:
ACN=Acetonitrile
AcOH=Acetic Acid
Cl=Chemical Ionization
DDQ=2,3-Dichloro-5,6-dicyano-1,4-benzoquinone
EI=Electron Impact
ESI=Electrospray Ionization
ISA=Isatoic Anhydride
LC/MS=Liquid Chromatography/Mass Spectroscopy
MeOH=Methanol
RT=Room Temperature
THF=Tetrahydrofuran
TFA=Trifluoroacetic Acid
VHL=Very High Load

What is claimed is:
1. A process for the synthesis of a compound or a library of compounds represented by Formula 1A and 1B:

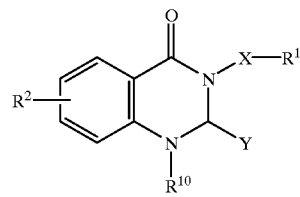

Formula 1A

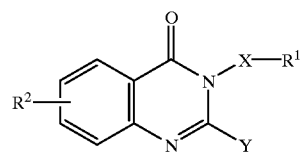

Formula 1B wherein:
$R^1$ is selected from a group consisting of —$C_{1-10}$ alkyl, —$OC_{1-4}$ alkyl, —$C_{1-4}$ saturated or partially unsaturated cyclo alkyl, heteroaryl, aryl substituted with $R^3$, $R^4$, and $R^5$, and —$C_{1-4}$ alkyl substituted with one or more of aryl or heteroaryl;

$R^2$ is selected from H, —$C_{1-4}$ alkyl, —COOH, —$COOC_{1-4}$ alkyl, —$NO_2$, —$NH_2$, —$C_{1-8}$ alkyl-C(O)—$NH_2$, —$NHC_{1-6}$ alkyl, aryl-C(O)—$NH_2$, 'CN, —O—$C_{1-4}$ alkyl, and halogen;

X represents —$(CH_2)_{1-4}$-;

Y represents —$C_{1-6}$ alkyl, —$C_{4-10}$ cycloalkyl, or aryl substituted with $R^6$, $R^7$, and $R^8$; $R^3$, $R^4$, and $R^5$ independently at each occurrence represent H, —$CF_3$, —$OCF_3$, halogen, —$OC_{1-4}$ alkyl or —$C_{1-6}$ alkyl;

$R^6$, $R^7$, and $R^8$ independently at each occurrence represent H, —O—$C_{1-4}$ alkyl, alkyl, —O—Ph—O-alkyl, —O—Ph-alkyl, —Ph, halogen, or —CN; alternatively when $R^6$ and $R^7$ along with the phenyl ring to which they are attached represent

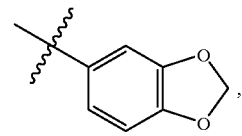

, $R^8$ is H; and
$R^{10}$ represents H, $C_1$–$C_4$ alkyl, benzyl, substituted benzyl, $C_2$–$C_6$ alkelene, substituted alkyl, or —$(CH_2)_{1-3}$-$COOC_{1-4}$ alkyl;

said process comprising the steps of:
(i) reacting an aldehyde of Formula A

Y—CHO                                Formula A with an amine of Formula B

[$R^2$]$R^1$-X—$NH_2$                       Formula B wherein [$R^2$]$R^1$, X, and Y are as defined above, to yield a compound of Formula C Formula C

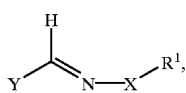

(ii) reacting the compound of Formula C with a compound of Formula D

Formula D

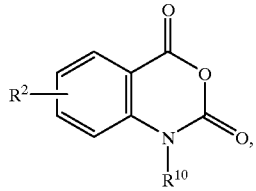

to yield a compound of Formula 1A

Formula 1A

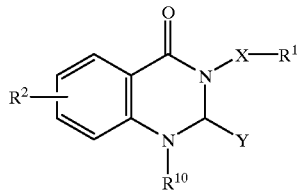

where $R^1$, $R^2$, $R^{10}$ and Y are as defined above; and
(iii) optionally oxidizing a compound of Formula 1A, when $R^{10}$ is H, followed by treating with an aminomethyl polystyrene resin, to yield a compound of Formula 1B.

2. A process of claim 1 wherein
step (i) comprises using acidic or protic solutions of the aldehyde of Formula A and the amine of Formula B;
step (ii) comprises reacting an acetic acid solution of a compound of Formula C with a solution of a compound of Formula D; and
step (iii) comprises oxidizing a compound of Formula 1A using iodine, $KMnO_4$, or $DDQ/CHCl_3$ suspension.

3. A process for synthesizing a compound or a library of compounds represented by Formula 1A:

Formula 1A

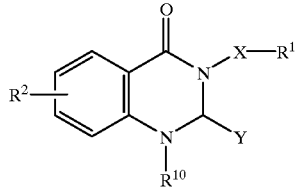

wherein:
$R^1$ is selected from a group consisting of $—C_{1-10}$ alkyl, $—OC_{1-4}$ alkyl, $—C_{4-10}$ saturated or partially unsaturated cyclo alkyl, heteroaryl, aryl substituted with $R^3$, $R^4$, and $R^5$, and $—C_{1-4}$ alkyl substituted with one or more of aryl or heteroaryl;
$R^2$ is selected from H, $—C_{1-4}$ alkyl, $—COOH$, $—COOC_{1-4}$ alkyl, $—NO_2$, $—NH_2$, $—C_{1-8}$ alkyl-C(O)—$NH_2$, $—NHC_{1-6}$ alkyl, aryl-C(O)—$NH_2$, $—CN$, $—O—C_{1-4}$ alkyl, and halogen;

X represents $—(CH_2)_{1-4}—$;
Y represents $—C_{1-4}$ alkyl, $—C_{4-10}$ cycloalkyl, or aryl substituted with $R^6$, $R^7$, and $R^8$;
$R^3$, $R^4$, and $R^5$ independently at each occurrence represent H, $—CF_3$, $—OCF_3$, halogen, $—OC_{1-4}$alkyl or $—C_{1-6}$ alkyl;
$R^6$, $R^7$, and $R^8$ independently at each occurrence represent H, $—O—C_{1-4}$ alkyl, alkyl, $—O—Ph—O$-alkyl, $—O—Ph$-alkyl, $—Ph$, halogen, or $—CN$; alternatively when $R^6$ and $R^7$ along with the phenyl ring to which they are attached represent

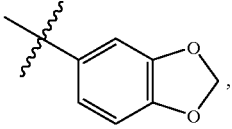

$R^8$ is H; and
$R^{10}$ represents H, $C_1$–$C_4$ alkyl, benzyl, substituted benzyl, $C_2$–$C_6$ alkelene, substituted alkyl, or $—(CH_2)_{1-3}$-$COOC_{1-4}$ alkyl;
said process comprising:
reacting a compound of Formula C Formula C

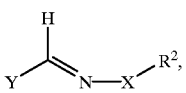

with a compound of Formula D

Formula D

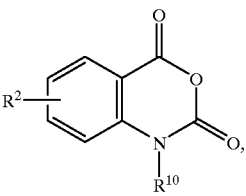

followed by optional treatment with an aminomethyl polystyrene resin, to yield a compound of Formula 1A Formula 1A

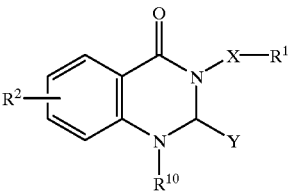

where $R^1$, $R^2$, $R^{10}$ and Y are as defined above.

4. A process of claim 1 wherein step (ii) comprises reacting an acetic acid solution of a compound of Formula C with a solution of a compound of Formula D.

5. A process of claim 4 wherein the solution of a compound of Formula D is prepared using at least one solvent selected from a group consisting of DMF, DMSO, dioxane, methylene chloride, acetic acid, chloroform, THF, and propionic acid.

6. A process of claim 5 wherein the solution of a compound of Formula D is prepared using at least one of acetic acid, methylene chloride, THF, and DMF.

19

7. A process of claim 6 wherein $R^1$ is selected from a group consisting of —$C_{1-6}$ alkyl, —$OC_{1-4}$ alkyl, —$C_{4-6}$ saturated or partially unsaturated cyclo alkyl, heteroaryl, aryl substituted with $R^3$, $R^4$, and $R^5$, or —$C_{1-4}$ alkyl substituted with one or more of aryl or heteroaryl;

$R^2$ is selected from H, —$C_{1-4}$ alky, —O—$C_{1-4}$ alkyl, and halogen;

Y represents —$C_{1-4}$ alkyl, or aryl substituted with $R^6$, $R^7$, and $R^8$;

$R^3$, $R^4$, and $R^5$ independently at each occurrence represent H, —O-$C_{1-4}$ alkyl, —$CF_3$, halogen, and —$C_{1-4}$ alkyl;

$R^6$, $R^7$, and $R^8$ independently at each occurrence represent H, —$C_{1-4}$ alkyl, —$C_{1-4}$ alkyl, —O—Ph—O—$C_{1-4}$ alkyl, —Ph, halogen, or when $R^6$ and $R^7$ along with the phenyl ring to which they are attached represent

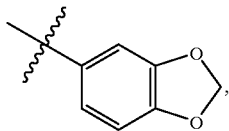

$R^8$ is H; and $R^{10}$ represents —$C_{1-2}$ alkyl, benzyl or —$CH_2$—COO—$C_2H_5$.

8. A process of claim 7 wherein $R^1$ represents

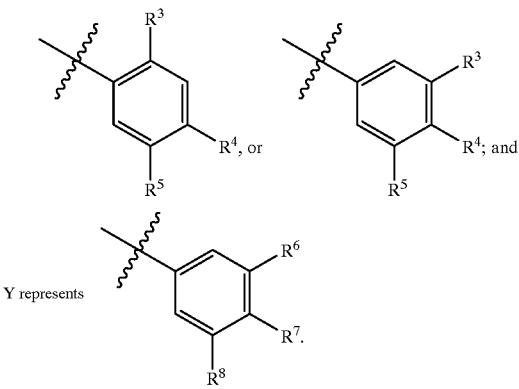

Y represents

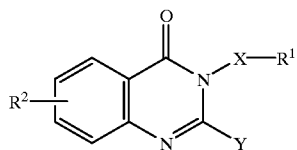

9. A process for synthesizing of a compound or a library of compounds of Formula 1B Formula 1B

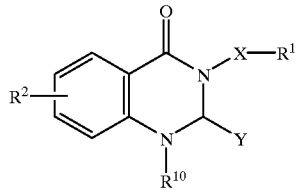

wherein:

$R^1$ is selected from a group consisting of —$C_{1-10}$ alkyl, —$OC_{1-4}$ alkyl, —$C_{4-10}$ saturated or partially unsatur

20 ated cyclo alkyl, heteroaryl, aryl substituted with $R^3$, $R^4$, and $R^5$, and —$C_{1-4}$ alkyl substituted with one or more of aryl or heteroaryl;

$R^2$ is selected from H, —$C_{1-4}$ alkyl, —COOH, —COO$C_{1-4}$ alkyl, —$NO_2$, —$NH_2$, —$CO_{1-8}$ alkyl-C(O)—$NH_2$, —$NHC_{1-6}$ alkyl, aryl-C(O)—$NH_2$, —CN, —O—$C_{1-4}$ alkyl, and halogen;

X represents —$(CH_2)_{1-4}$-;

Y represents —$C_{1-6}$ alkyl, —$C_{4-10}$ cycloalkyl, or aryl substituted with $R^6$, $R^7$, and $R^8$;

$R^3$, $R^4$, and $R^5$ independently at each occurrence represent H, —$CF_3$, —$OCF_3$, halogen, —$OC_{1-4}$ alkyl or —$C_{1-6}$ alkyl;

$R^6$, $R^7$, and $R^8$ independently at each occurrence represent H, —O—$C_{1-4}$ alkyl, alkyl, —O—Ph—O-alkyl, —O—Ph-alkyl, —Ph, halogen, or —CN; alternatively when $R^6$ and $R^7$ along with the phenyl ring to which they are attached represent

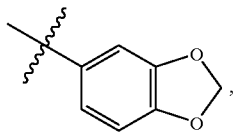

$R^8$ H; and $R^{10}$ represents H;

said process comprising:
  oxidizing a compound of Formula 1A,

Formula 1A wherein X, Y, $R^1$, $R^2$, and $R^{10}$ are as defined above, followed by treating with an aminomethyl polystyrene resin, to yield a compound of Formula 1B.

10. A process of claim 9 which comprises oxidizing a compound of Formula 1A using iodine, $KMnO_4$, or DDQ/$CHCl_3$ suspension.

11. A process of claim 10 wherein $R^1$ is selected from a group consisting of —$C_{1-6}$ alkyl, —$OC_{1-4}$ alkyl, —$C_{4-6}$ saturated or partially unsaturated cyclo alkyl, heteroaryl, aryl substituted with $R^3$, $R^4$, and $R^5$, or —$C_{1-4}$ alkyl substituted with one or more of aryl or heteroaryl;

$R^2$ is selected from H, —$C_{1-4}$ alkyl, —O—$C_{1-4}$ alkyl, and halogen;

Y represents —C$_{1-4}$ alkyl, or aryl substituted with R$^6$, R$^7$, and R$^8$;

R$^3$, R$^4$, and R$^5$ independently at each occurrence represent H, —O—C$_{1-4}$ alkyl, —CF$_3$, halogen, and —C$_{1-4}$ alkyl;

R$^6$, R$^7$, and R$^8$ independently at each occurrence represent H, —O—C$_{1-4}$ alkyl, —C$_{1-4}$ alkyl, —O—Ph—O—C$_{1-4}$ alkyl, —Ph, halogen, or when R$^6$ and R$^7$ along with the phenyl ring to which they are attached represent

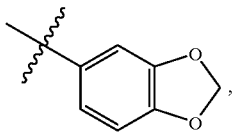
,

R$^8$ is H.

12. A process of claim 11 wherein R$^1$ represents

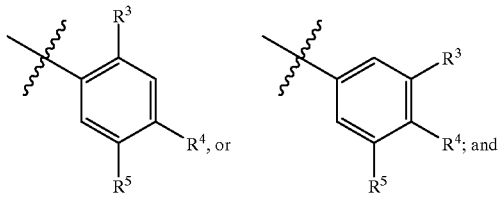

Y represents

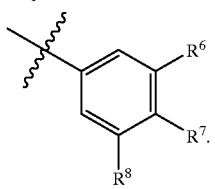
.

* * * * *